United States Patent [19]
Shi et al.

[11] Patent Number: 6,103,924
[45] Date of Patent: Aug. 15, 2000

[54] PROCESS FOR THE PREPARATION OF 2,3, 5-TRIMETHYLHYDROQUINONE DIESTERS

[75] Inventors: Nongyuan Shi, Hainburg; Mario Scholz, Gründau; Steffen Hasenzahl, Maintal; Horst Weigel, Rodenbach; Bernd Drapal, Alzenau; Ralph McIntosh, Hanau; Hans J. Hasselbach; Klaus Huthmacher, both of Gelnhausen, all of Germany

[73] Assignee: Degussa-Huls AG, Frankfurt am Main, Germany

[21] Appl. No.: 09/295,359

[22] Filed: Apr. 21, 1999

[30] Foreign Application Priority Data

Apr. 21, 1998 [DE] Germany .......................... 198 17 644

[51] Int. Cl.⁷ .................................................. C07C 67/48
[52] U.S. Cl. ............................................. 560/79; 560/231
[58] Field of Search ..................... 560/79, 231; 568/763, 568/341

[56] References Cited

U.S. PATENT DOCUMENTS

| | | | |
|---|---|---|---|
| T900,015 | 7/1972 | Thwcatt | 260/621 |
| 4,247,720 | 1/1981 | Baudouin | 568/772 |
| 5,908,956 | 6/1999 | Takahashi | 560/79 |

FOREIGN PATENT DOCUMENTS

| | | |
|---|---|---|
| 0 850 910 A1 | 7/1998 | European Pat. Off. . |
| 0916642 | 5/1999 | European Pat. Off. . |
| 2 149 159 | 4/1972 | Germany . |
| 26 46 172 | 4/1977 | Germany . |
| 196 27 977 A1 | 11/1997 | Germany . |

Primary Examiner—Ardin H. Marschel
Assistant Examiner—Sherif Kafafi
Attorney, Agent, or Firm—Pillsbury Madison & Sutro LLP

[57] ABSTRACT

Preparation of 2,3,5-trimethylhydroquinone diesters by rearrangement of 2,6,6-trimethylcyclohex-2-ene-1,4-dione (4-oxo-isophorone, ketoisophorone) in the presence of a solid, acid catalyst and an acylating agent, for example carboxylic acid anhydrides or carboxylic acid halides. The 2,3,5-trimethylhydroquinone diester may then optionally be saponified to the free 2,3,5-trimethylhydroquinone, which is a valuable building block in the synthesis of vitamin E.

21 Claims, No Drawings

PROCESS FOR THE PREPARATION OF 2,3,5-TRIMETHYLHYDROQUINONE DIESTERS

CROSS-REFERENCE TO RELATED APPLICATIONS

This application is based on DE 198 17 644.9, filed Apr. 21, 1998, the disclosure of which is incorporated herein by reference.

FIELD OF THE INVENTION

The present invention relates to a new process for the preparation of 2,3,5-trimethylhydroquinone diesters by rearrangement of 2,6,6-trimethylcyclohex-2-ene-1,4-dione (4-oxo-isophorone, ketoisophorone) in the presence of a solid, acid catalyst and an acylating agent, for example carboxylic acid anhydrides, carboxylic acid halides. The 2,3,5-trimethylhydroquinone diester may optionally then be saponified to the free 2,3,5-trimethylhydroquinone, which is a valuable building block in the synthesis of vitamin E.

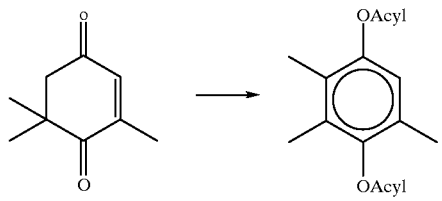

BACKGROUND OF THE INVENTION 2,3,5-trimethylhydroquinone (TMHQ) is an important intermediate that is used in the production of vitamin E and vitamin E acetate. In addition to the known preparation processes from aromatic starting materials, 2,3,5-trimethylhydroquinone can be prepared from a non-aromatic compound, namely 2,6,6-trimethylcyclohex-2-ene-1,4-dione, by rearrangement under acylating conditions followed by hydrolysis.

Patent Specification DE 26 46 172 C2 describes a process in which 2,6,6-trimethylcyclo-hex-2-ene-1,4-dione is directly rearranged in the vapor phase at elevated temperature in contact with an acid catalyst to form trimethyl-hydroquinone. The yield in this process is however low (50% at 30% conversion). If the aromatization of 2,6,6-trimethylcyclohex-2-ene-1,4-dione is carried out in the presence of an acylating agent, then trimethylhydroquinone diesters are obtained that yield trimethylhydroquinone on subsequent hydrolysis.

According to Bull. Korean Chem. Soc. 1991, 12, 253, for example, the rearrangement is carried out in 5% solution acetic anydride by adding five equivalents of concentrated sulfuric acid. The trimethylhydroquinone diester is in this case obtained only in a 30% yield.

In a further process according to DE-OS 2 149 159, 2,6,6-trimethylcyclohex-2-ene-1,4-dione can be converted in the presence of acetic anhydride in a proton-catalyzed or Lewis acid-catalyzed rearrangement to form trimethylhydroquinone diacetate, which is then saponified to trimethylhydroquinone. Moderate to good yields are said to be obtained in this process.

From DE-OS 196 27977, it is known to prepare TMHQ by reacting ketoisophorone with an acylating agent in the presence of very strong acids, for example fluorosulfonic acid or oleum. In this process the initially formed corresponding ester is then saponified.

The known processes have the disadvantage that either the yields are low or that corrosion problems arise at the same time due to the use of strong dissolved acids, which make it necessary to use high quality materials. The separation and recycling of the dissolved catalyst are also difficult to carry out.

SUMMARY OF THE INVENTION

The object of the invention is to provide a process for the preparation of 2,6,6-trimethylcyclohex-2-ene-1,4-dione diesters that avoids the disadvantages of the known processes. The corresponding hydroquinones may optionally be obtained from the esters by hydrolysis.

It has been found that 2,6,6-trimethylcyclohex-2-ene-1,4-dione can be converted in the presence of a solid acid with an acylating agent to form a trimethylhydroquinone diester. 2,3,6-Trimethylhydroquinone is obtained by an optional subsequent saponification.

All acid-acting solids that are stable under the reaction conditions may in principle be used for the process according to the invention. Examples of such substances are crystalline and/or amorphous aluminosilicates, clay minerals or Pillard clays that are used in each case in the H-form, mineral acids on suitable supports, for example 158 sulfuric acid on $ZrO_2$ or $SnO_2$, or phosphoric acid on $SiO_2$, ion exchange resins with acidic groups, in particular based on fluorinated resins such as Nafion-H® (duPont) or Amberlyst® (Rohm and Haas), as well as polysiloxanes with acidiyc groups, for example Deloxan ASP® (Degussa-Huls AG) $SO_3$ groups in particular serve as acidic groups.

Particularly suitable are acidic, large pore (with 12 annular pores) zeolites with pore diameters of between 0.5 and 0.8 nm. Examples include Y-zeolites, beta-zeolites, dealuminated zeolites or mordenites. These are described in particular in "Atlas of Zeolite Structure Types" (W. M. Meier et al., 4th Revised Edition, Elsevier, 1996), incorporated by reference herein. In principle acidic zeolite types having the above or larger pore diameters are suitable. Also suitable are medium pore (with 10 annular pores) zeolites, for example of the ZSM-5 type.

The modulus, i.e. the $SiO_2/Al_2O_3$ molar ratio of a zeolite, which is an important measure of its acid capacity, may vary within wide limits. The modulus of a given zeolite type may be determined basically by the composition of the synthesis gel from which it is crystallized. In the case of the Y-zeolites this can also be adjusted in a wide range by the subsequent dealumination, for example by reaction with steam or $SiCl_4$. Conventional zeolite syntheses, as ore described, for example, in "Handbook of Molecular Sieves" (R. Szostak, Van Nostrand Reinhold, 1992) and literature cited therein, yield the zeolites generally in the catalytically inactive Na-form. In order to convert them into the catalytically active H-form, an ion exchange may be carried out with acids, for example hydrochloric acid or sulfuric acid, or with ammonium salts, for example $NH_4Cl$, $(NH_4)_2SO_4$ or $NH_4$-acetate, followed by calcination.

Suitable above all for the process according to the invention are H-Y-zeolites with a modulus between 7.5 and 200, in particular between 25 and 120, H-beta-zeolites with a modulus between 13 and 60, in particular between 18 and 30, and H-mordenites with a modulus between 5 and 100, in particular between 10 and 30.

Materials also suitable for the process according to the invention are aluminosilicates discovered during the last few years, having a regular mesopore structure, for example MCM-41 or MCM-48. The mesopores with pore diameters between 2.0 and 10.0 nm permit a rapid diffusion of the reactants to the catalytically active centers.

The zeolites or aluminosilicates with regular mesopore structure may be used in shaped or unshaped form in the process according to the invention. The unshaped materials are obtained directly after the synthesis and a possible ion exchange. The shaping may be carried out directly after the synthesis, by known methods such as granulation for example by spray drying, fluidized bed—spray granulation drying, or plate granulation, extrusion as well as tabletting. Examples of possible binders that may be added in the shaping step are silicon dioxide, aluminum oxide, titanium dioxide and clay minerals. In the process according to the invention there may be used in particular shaped bodies in the fixed bed process, or granulates in the suspension process.

The materials used as catalysts generally lose their catalytic activity during the reaction. The reason for this is in particular the deposition of high molecular weight secondary products or by-products in the pore system. In order to restore the original activity these products must be removed by suitable methods. This can be achieved in the case of inorganic materials for example by calcination in a muffle furnace, a rotating cylinder or any other suitable equipment, at a temperature between 250° and 800° C., preferably between 400° and 650° C. The calcination is generally carried out in an air or inert gas atmosphere.

It is particularly advantageous to carry out the calcination first of all in a nitrogen atmosphere and afterwards in air. The calcination duration can easily be matched to the specific conditions, a duration of 2 h generally being sufficient. The heating rate may vary within a wide range. If no or only slight amounts of high molecular weight products have been formed, the regeneration may also be carried out by means of an extraction using suitable solvents. Suitable solvents for this purpose are, for example, esters, such as ethyl acetate; ketones, such as acetone; organic acids, acetic acid; acid anhydrides, such as acetic anhydride, or alcohols. In this case the catalyst to be regenerated is stirred with the corresponding solvent at room temperature or elevated temperature. The solid is then separated, for example by filtration or centrifugation, if necessary dried, calcined, and returned to the process.

Besides zeolites and aluminosilicates, other solid acids that are stable under the acylating conditions are also suitable. Examples of such acids are mineral acids on suitable carriers, but also polymers that contain strong acidic groups. Preferred among this group is Nafion-H® from duPont, which is a perfluorinated sulfonic acid group-containing polymer that is particularly thermally and chemically resistant. Particularly preferred in this connection is a modification with a large surface, formed by silicone crosslinking (M. A. Harmer, *J. Am. Chem. Soc.*, 118, 1996, 7709).

The amount of catalyst used is between 5 and 150 wt. % referred to 2,6,6-trimethylcyclohex-2-ene-1,4-dione, preferably between 20 and 60 wt. % referred to 2,6,6-trimethylcyclohex-2-ene-1,4-dione.

The rearrangement takes place conveniently at temperatures between about 0° and 140° C., preferably between about 20° and 100° C.

The acylating agent used according to the invention is preferably a carboxylic acid anhydride, an enol ester or a carboxylic acid chloride. In particular a carboxylic acid anhydride of the general formula I is used

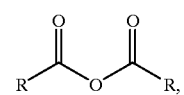

(I)

in which R denotes an optionally substituted aliphatic, alicyclic or aromatic radical with 1–8 carbon atoms, which optionally contains 1 to 3 halogen atoms. In particular the anhydrides of acetic acid, propionic acid, butyric acid, isobutyric acid, cyclohexane carboxylic acid, benzoic acid and chloroacetic acid are suitable. Particularly suitable is acetic anhydride. Instead of the acid anhydrides, other acylating agents may also be used, for example enol esters or acyl halides.

Examples of suitable acyl halides are acetyl chloride, propionyl chloride and butyryl chloride. Enol esters such as vinyl acetate, isopropenyl acetate and isopropenyl isobutyrate serve as acylating agents in the presence of catalysts and are especially suitable for carrying out the claimed process. As acylating agents suitable enol esters correspond to the general formula

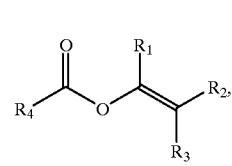

(II)

in which $R_1$ and $R_2$ denote hydrogen atoms or alkyl radicals with 1 to 8 carbon atoms or alkylene radicals with 1 to 5 carbon atoms, which together form a 5- or 6- membered carbon ring, $R_3$ denotes a hydrogen atom or an alkyl radical with 1 to 8 carbon atoms, and $R_4$ denotes an aliphatic, alicyclic or aromatic hydrocarbon radical with 1 to 8 carbon atoms.

The molar ratio of the acylating agent to 2,6,6-trimethylcyclohex-2-ene-1,4-dione may vary. In a reaction without additional solvent the molar ratio of acylating agent to 2,6,6-trimethylcyclohex-2-ene-1,4-dione should be between 3:1 and 10:1, preferably between 3:1 and 5:1. The excess acylating agent serves as solvent, which can be recovered by distillation after separating the solid catalyst.

The rearrangement may also take place in the presence of organic solvents. Suitable organic solvents are aliphatic and cyclic esters, for example ethyl acetate, propyl acetate, isopropyl acetate, isobutyl acetate and □-butyrolactone; hydrocarbons, for example hexane, heptane, toluene, and xylene; and ketones, for example isobutyl methyl ketone, diethyl ketone and isophorone.

By adding one of the aforementioned solvents the amount of acylating agent can be reduced. The molar ratio employed according to the invention between the acylating agent and ene dione is then preferably between 2:1 and 3:1.

DETAILED DESCRIPTION OF THE PREFERRED EMBODIMENTS

EXAMPLE 1

15.2 g (0.1 mole) of 2,6,6-trimethylcyclohex-2-ene-1,4-dione were added at 30° to 40° C. to a suspension of 51.1 g (0.5 mole) of acetic anhydride and 6.2 g of H-Y-zeolite ($SiO_2/Al_2O_3$ modulus=25±5, activated for 2 h at 400° C.) This mixture was stirred for 5 h at 60° to 100° C., the progress of the reaction being followed by HPLC. After completion of the reaction the reaction mixture was cooled to room temperature and the catalyst was removed by filtration. The filtrate, which consists of acetic acid, unreacted acetic anhydride as well as dissolved trimethylhydroquinone diacetate, was evaporated to dryness under reduced pressure at 60°C in a rotary evaporator. The residue was taken up in 150 ml of water, homogenized in a mortar, and the pH of the suspension was adjusted to 5–6 with caustic soda. The trimethylhydroquinone diacetate thereby obtained was suction filtered, washed with water, and dried in vacuo. The yield was 22.5 g, corresponding to 95% of theory.

EXAMPLE 2

7.7 g of H-Y-zeolite ($SiO_2/Al_2O_3$ modulus=25±5, activated for 2.5 h at 450° C.) were suspended while stirring in 50 ml of toluene, and stirred with 30.6 g (0.3 mole) of acetic anhydride and 15.2 g (0.1 mole) of 2,6,6-trimethylcyclohex-2-ene-1,4-dione for 7 h at 90° to 110° C. After completion of the reaction the catalyst was filtered off and washed with toluene. The filtrate was evaporated to dryness under reduced pressure at 60° C. in a rotary evaporator. The residue was dissolved in 20 ml of acetic acid and added to 100 ml of water. The pH of the suspension was adjusted to 6 with caustic soda. The precipitated trimethylhydroquinone diacetate was suction filtered, washed with water, and dried in vacuo. The yield was 22.4 g, corresponding to 95% of theory.

EXAMPLE 3

The procedure was the same as in Example 2, except that n-propyl acetate was used instead of toluene as solvent. The yield was 22.3 g, corresponding to 95% of theory.

EXAMPLE 4

15.2 g (0.1 mole) of 2,6,6-trimethylcyclohex-2-ene-1,4-dione was quickly added to a suspension of 7.8 g of H-Y-zeolite ($SiO_2/Al_2O_3$ modulus=120±20, activated for 1 h at 450° C.) and 76.6 g (0.75 mole) of acetic anhydride. The mixture was heated to 95° C. and stirred for 3 h. The mixture was then cooled to room temperature and worked up in a similar manner to Example 1. The yield was 23.0 g, corresponding to 97% of theory.

EXAMPLE 5

In a similar manner to Example 4, 7.4 g of H-Y-zeolite ($SiO_2/Al_2O_3$ modulus=55±10, activated for 1 h at 450°C) were suspended in 76.6 g (0.75 mole) of acetic anhydride and 15.2 g (0.1 mole) of 2,6,6-trimethylcyclohex-2-ene-1, 4-dione were quickly added. After reaction for 3 hours at 30° C. to 90° C. and working up as described in Example 1, the yield was 23.0 g, corresponding to 97% of theory.

EXAMPLE 6

10.0 g of H-beta-zeolite ($SiO_2/Al_2O_3$ modulus=27, activated for 2 h at 150° C.) were suspended in 30.7 g (0.3 mole) of acetic anhydride and 15.3 g (0.1 mole) of 2,6,6-trimethylcyclohex-2-ene-1,4-dione were added. The mixture was stirred for 48 h at 140° C. and then worked up as in Example 1. The yield was 22.1 g, corresponding to 94% of theory.

EXAMPLE 7

15.5 g of MCM-41 ($SiO_2/Al_2O_3$ modulus=25, activated for 1 h at 150° C.) were suspended in 76.6. g (0.75 mole) of acetic anhydride and 15.3 g (0.1 mole) of 2,6,6-trimethylcyclohex-2-ene-1,4-dione were added. The mixture was stirred for 21 h at 140° C. and then worked up as in Example 1. The yield was 20.4 g, corresponding to 86% of theory.

EXAMPLE 8

15.2 g (0.1 mole) of 2,6,6-trimethylcyclohex-2-ene-1,4-dione were added dropwise at 50° C. within 15 minutes to a stirred suspension of 30.6 g (0.30 mole) of acetic anhydride and 1.52 g of Nafion® $NR_{50}$ (10–35 mesh). The suspension was stirred for 2 h at 50° C. and 3 h at 80° C. The catalyst was removed by filtration and the 2,6,6-trimethylcyclohex-2-ene-1,4-dione and trimethylhydroquinone diacetate in the filtrate were measured by HPLC. The results showed a conversion of 93.1% and a yield of 85.1% of theory.

EXAMPLE 9

A silicone-crosslinked Nafion® was used as catalyst, which was prepared according to the directions given in the article by Mark A. Harmer in *J. Am. Chem. Soc.*, 118, 1996, 7709. 15.2 g (0.10 mole) of 2,6,6-trimethylcyclohex-2-ene-1,4-dione were stirred at 40° C. within 15 minutes into a suspension of 3.1 g of this catalyst and 30.6 g (0.30 mole) of acetic anhydride, the temperature rising to 51° C. After 5 h at 50° C. the conversion was 96%. After working up in the same way as described in Example 1, 22.1 g of product was obtained, corresponding to a yield of 92.2% of theory.

EXAMPLE 10

Example 9 was repeated, the amount of catalyst being increased to 4.5 g. After a reaction time of 3 h at 50° C. the conversion of 2,6,6-trimethylcyclohex-2-ene-1,4-dione was 96.1%. The catalyst was filtered off, washed with 10 ml of acetic acid, and reused together with 0.5 g of fresh catalyst in the rearrangement. After a reaction time of 3.5 h the conversion was 95.8%.

What is claimed is:

1. A process for the preparation of 2,3,5-trimethylhydroquinone diesters comprising:
   carrying out a rearrangement of 2,6,6-trimethylcyclohex-2-ene-1,4-dione in the presence of an acylating agent and an acid, whereby the rearrangement occurs in a liquid phase in the presence of a solid, acid catalyst;
   separating the solid acid catalyst to obtain 2,3,5-trimethylhydroquinone diester,
   regenerating the solid acid catalyst by, optionally, drying, and then calcinating the solid acid catalyst.

2. The process according to claim 1, wherein the catalyst comprises at least one member selected from the group consisting of crystalline aluminosilicates, amorphous aluminosilicates, clay minerals and Pillard clays, in each case in the H-form.

3. The process according to claim 2, wherein the catalyst comprises an acid zeolite with a pore diameter of 0.5 to 0.8 nm.

4. The process according to claim 3, wherein the catalyst comprises at least one member selected from the group consisting of zeolites of the types Y, beta or ZSM5, dealuminated zeolites or mordenites.

5. The process according to claim 3, wherein the catalyst comprises a mesoporous molecular sieve.

6. The process according to claim 3, wherein the mesoporous molecular sieve has a MCM-41 or MCM-48 structure.

7. The process according to claim 1, wherein the catalyst comprises ion exchange resins or polysiloxane compounds that carry acidic groups.

8. The process according to claim 1, wherein the catalyst comprises mineral acids on inorganic carriers.

9. The process according to claim 1, comprising:
using the solid acid catalyst in an amount of 5 to 150 wt. % with reference to the 2,6,6-trimethylcyclohex-2-ene-1,4-dione.

10. The process according to claim 9, comprising:
using the catalyst in an amount of 20 to 60%.

11. The process according to claim 1, comprising:
using as acylating agent a carboxylic acid anhydride of the general formula (1):

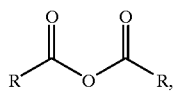

(I)

in which R denotes an optionally substituted aliphatic, alicyclic or aromatic radical with 1 to 8 carbon atoms.

12. The process according to claim 11, wherein the carboxylic acid anhydride comprises acetic anhydride.

13. The process according to claim 1, wherein the acylating agent comprises a carboxylic acid halide.

14. The process according to claim 1, wherein the acylating agent comprises an enol ester of the general formula (II):

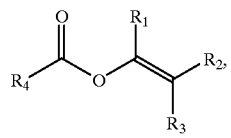

(II)

in which $R_1$ and $R_2$ denote hydrogen atoms, alkyl radicals with 1 to 8 carbon atoms, or alkylene radicals with 1 to 5 carbon atoms, which together form a 5- or 6-membered ring, $R_3$ denotes a hydrogen atom or an alkyl radical with 1 to 8 carbon atoms and $R_4$ denotes an aliphatic, alicyclic or aromatic radical with 1 to 8 carbon atoms.

15. The process according to claim 1, wherein the acylating agent and the 2,6,6-trimethylcyclohex-2-ene-1,4-dione are used in a molar ratio of 2:1 to 20:1.

16. The process according to claim 15, wherein the molar ratio is 2:1 to 5:1.

17. The process according to claim 1, comprising:

carrying out the reaction at a temperature from 0° to 150° C.

18. The process according to claim 17, wherein the temperature is 20° to 100° C.

19. The process according to claim 1, further comprising:

carrying out the rearrangement in the presence of an organic solvent.

20. The process according to claim 1, further comprising:

carrying out the rearrangement in the presence of an organic solvent, wherein the acylating agent and the 2,6,6-trimethylcyclohex-2-ene-1,4-dione are used in a molar ratio of 2:1 to 3:1.

21. The process according to claim 1, further comprising:

saponifying the 2,3,5-trimethylhydroquinone diester obtained to form 2,3,5-trimethylhydroquinone.

* * * * *